United States Patent [19]

Sirbasku et al.

[11] Patent Number: 4,670,539
[45] Date of Patent: Jun. 2, 1987

[54] PEPTIDE GROWTH FACTORS DERIVED FROM ESTROGEN RESPONSIVE KIDNEY TISSUE

[75] Inventors: David A. Sirbasku, Houston, Tex.; Tatsuhiko Ikeda, Kobe, Japan

[73] Assignee: Board of Regents, The University of Texas, Austin, Tex.

[21] Appl. No.: 635,220

[22] Filed: Jul. 27, 1984

[51] Int. Cl.$^4$ .............................................. C07K 7/10
[52] U.S. Cl. .................................................... 530/324
[58] Field of Search ........................................ 530/324

[56] References Cited

PUBLICATIONS

Ikeda, T. et al., "Isolation and Properties of Endocrine and Autocrine Type Mammary Tumor Cell Growth Factors (Estromedins) in: Proceedings of the Second International Congress on Hormones and Cancer," (F. Bresciani et al., ed.), Raven Press, New York, pp. 171–186, (1984).

Primary Examiner—Delbert R. Phillips
Attorney, Agent, or Firm—Arnold, White & Durkee

[57] ABSTRACT

Two forms of polypeptide growth factors have been purified to homogeneity from lyophilized powder of mature ewe kidneys. From 500 g of powder 8 to 14 mg of kidney derived growth factor (KDGF) was isolated. An 18,000 fold purification was accomplished with a 4 to 7% yield by a 6 step procedure that included an initial acetic acid extraction, heating at 95°, Bio-Rad AG50W X8 cation exchange chromatography, 2 sequential DEAE-Sepharose CL-6B anion exchange steps at pH 5.8 and 6.2, respectively, and finally Sephadex G-50 chromatography in 0.1M acetic acid. From the Sephadex molecular sieve separation, the KDGF activity eluted in the same fractions as the single protein peak. Polyacrylamide gel electrophoresis analysis under non-reducing and non-denaturing conditions followed by Coomassie Blue staining confirmed a single band having a $M_r$ 4,200. Molecular sieve HPLC done under acidic conditions confirmed a similar high (i.e. greater than 95%) degree of homogeneity. This preparation of KDGF was shown to be mitogenic for rat pituitary tumor cells, and hamster and rat kidney tumor cells, but not for normal rat diploid fibroblasts or low passage normal rat kidney (NRK) cells. The KDGF preparation that appeared greater than 90% homogeneous by the criteria described above was separated by chromatofocusing into 2 forms, KDGF-I and KDGF-II, of pI 5.2 and 4.8, respectively. Both forms showed $M_r$ 4200. KDGF-II was the more abundant form, being 70% of the total KDGF isolated from the chromatofocusing elution. The $G_{50s}$ of KDGF-I and KDGF-Ii were 10 ng/ml ($2.38 \times 10^{-9}$M) and 19 ng/ml ($4.52 \times 10^{-9}$M), respectively, with the MTW9/PL cells in culture without any other additions to the serum free medium used in these bioassays.

3 Claims, 5 Drawing Figures

PEPTIDE GROWTH FACTORS DERIVED FROM ESTROGEN RESPONSIVE KIDNEY TISSUE

BACKGROUND OF THE INVENTION

The present invention relates to peptide growth factors and their purification from biological tissue. More particularly, the invention is directed to the purification and characterization of low molecular weight (<10,000) peptide growth factors derived from estrogen responsive tissue.

The Government may have rights in this invention pursuant to a funding agreement sponsored by a National Cancer Institute Grant, No. RO1-CA-26617, and an American Cancer Society Grant, No. BC-255.

Polypeptide growth factors have been isolated from organs of various animal species, noncellular plasma fractions, cellular elements of the blood, and cells growing in culture; these activities have been implicated in mammalian cell growth in vivo and in vitro. Several of these mitogens have been purified to homogeneity by procedures that utilize extraction into acidic pH solutions and/or treatment at high temperatures to remove major impurities. The mitogenic species isolated by these methods show molecular weights ranging from 6,000 to 63,000 and primary structures consisting of either one polypeptide chain or two polypeptide chains covalently attached by disulfide bonds.

Major members of the acid-stable family of growth factors are:
1. EGF, epidermal growth factor;
2. MSA, multiplication stimulating activity;
3. IGF I and IGF II, insulin-like growth factors I and II, respectively;
4. SmC, somatomedin C;
5. PDGF, platelet-derived growth factor;
6. TGF, transforming growth factor; and
7. SGF, Sarcoma growth factor.

While, to some degree, members of this group share common properties (i.e. insulin-like responses of IGF I and IGF II), most are distinct molecular entities which, in some cases, interact with different specific cell-surface receptors and in other cases interact with a common receptor.

The role of estrogen inducible growth factors in estrogen responsive growth of mammary tumor cells was first proposed circa 1978. At that time, estrogens were proposed to induce some target tissues to synthesize and/or secrete polypeptide growth factors to enter the circulation and promote the growth of distant mammary target tissue tumors. Potential tissue sources for such factors have been identified as uterus, kidney and pituitary. Investigators designated these growth factors "estromedins" to indicate their role as mediators of the estrogenic growth effects in vivo.

Previously, estrogen responsive tumor cell growth factor activity has been identified in extracts of uteri and kidneys obtained from estrogen-treated rats. Initially, applicants conducted studies to determine whether these organs might be the possible sources of mammary/pituitary cell growth factor activities found in plasma and serum, and to determine whether these activities have a role in the estrogen-responsive growth of mammary and pituitary tumors in vivo. Preliminary data showed that MTW9/PL rat mammary and GH3/C14 rat pituitary tumor cells grew (as measured by cell number increase) in serum free medium supplemented with only u/ml quantities of crude extracts of rat uteri or kidneys.

Since these studies were conducted with heterogeneous preparations, several important questions remained to be resolved. First, the question of whether these growth effects were due to the combination of several relatively non-specific growth and/or survival promoters was unresolved. It seemed possible that more than one mitogenic activity might have been present in the crude extracts, and that together these were responsible for our observed mitogenic effects. Second, the initial observations did not resolve whether the growth factor(s) extracted from the kidney was the same as that extracted from the uterus. Our studies suggested molecular differences since extracts of rat uteri contained an approximately 20 times higher specific activity than identical preparations of rat kidney did, although such differences could have also been related to total growth factor content and not to specific molecular properties.

Applicants in their copending application, Ser. No. 597,980, filed Apr. 6, 1984 have previously described purified peptide growth derived from estrogen responsive uterine and pituitary tissue. The present invention provides separate but related purified peptide growth factors derived from estrogen responsive kidney tissue.

SUMMARY OF THE INVENTION

The present invention provides two forms of polypeptide growth factors derivable from estrogen responsive kidney tissue. The two growth factors of this invention are termed herein KDGF-I and KDGF-II. Both KDGF-I and KDGF-II are heat and acid stable, have a molecular weight of approximately 4200±200 daltons and exhibit a PI of 5.2±0.2 and 4.8±0.2 respectively. KDGF-II is the more abundant form of the two when extracted from mature ewe kidneys. By the methods provided by this invention the growth factors are purified to substantial homogeneity. Substantial homogeneity as used herein is 90% or greater purity of the growth factor and substantially all of the protein content is responsible for the assessed biological growth activity.

The present invention further provides methods for obtaining KDGF-I and KDGF-II from estrogen responsive kidney tissue. The kidney growth factors KDGF-I and KDGF-II are purified to substantial homogeneity from kidney tissue by a six-step method comprising: (1) extracting kidney tissue with an aqueous solution of dilute acid; (2) heating the extract to remove proteolytic activity and other major impurities; (3) subjecting the extract to cation exchange chromatography; followed by (4,5) two sequential anion exchange steps at pH 5.8 and 6.2, respectively; and finally (6) separating for the resultant extracted material a 3000-6000 molecular weight fraction using molecular sieve chromatography. From the molecular sieve separation, both KDGF activity forms are eluted in the same fractions as a single protein peak. Chromatofocusing the collected KDGF activity yields the two separate forms KDGF-I and KDGF-II.

BRIEF DESCRIPTION OF THE DRAWINGS

FIG. 5 - 8 M urea, 0.1% SDS 12.5% PAGE and Coomassie blue staining analysis of the KDGF step 6 preparation. The gel on the left shows the migration positions of horse heart myoglobin and fragments of myoglobin of known $M_r$.

DETAILED DESCRIPTION OF THE PREFERRED EMBODIMENTS OF THE INVENTION

Figure 1:
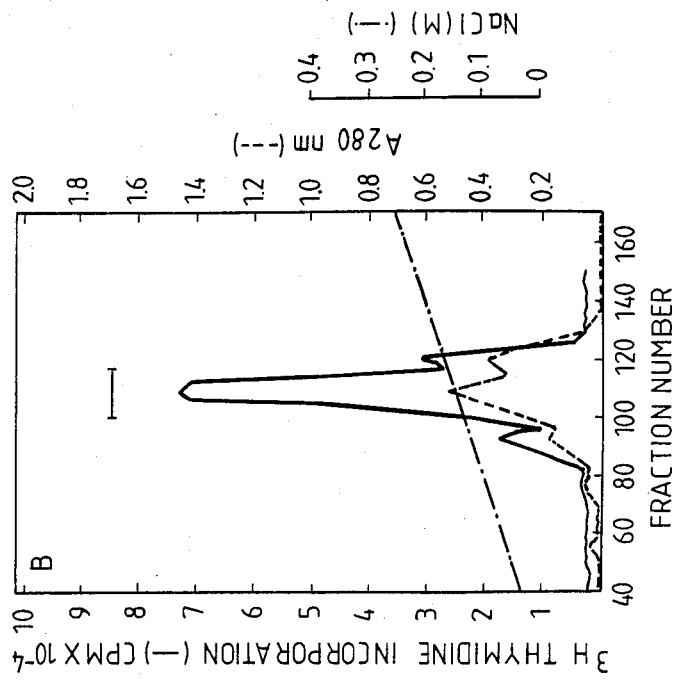
FIG. 1 - Elution profile of KDGF activity and protein from the DEAE-Sepharose CL-6B column equilibrated at pH 5.8 and eluted with a linear sodium chloride gradient.

The following discussion relating to purification of kidney derived peptide growth factors is in the terms of the preferred embodiments of this invention, which respresents the best mode known to the inventors at the time of this application.

The activity of peptide growth factors derived from estrogen responsive tissue (estromedins) is exemplified by induction of mammary tumor growth. A model system to assay for estromedin activity uses MTW9/PL rat mammary tumor cells. In brief, the cultured MTW9/PL cells are exposed to growth factor. The degree of cell growth activity was measured by the amount of $^3H$-thymidine cellular uptake.

Experimental Procedures Demonstrating Biological Activity of Estrogen Inducible Growth Factors Cell Cultures The MTW9/PL rat mammary tumor cell line used in this study was established in culture from the estrogen- and prolactin-responsive MTW9A tumor by methods described previously. Sirbasku, D. A. *Cancer, Research*, 38:1154-1165 (1978). MTW9/PL cell growth in culture is thyroid hormone, pituitary factor responsive, and estrogen responsive. The MTW9/PL cells were assayed periodically for the ability to form estrogen-responsive tumors in vivo as described previously; after more than 6 years in culture, the cells still demonstrate the same hormone-responsive tumor formation properties described in the original report.

Stock cultures of MTW9/PL cells were maintained in the formulation of DME medium prepared at the higher (4.5 g/liter) concentration of glucose and supplemented with 2 mM glutamine, 240 $\mu g/ml$ of potassium penicillin G, 540 $\mu g/ml$ of streptomycin sulfate, 50 $\mu g/ml$ of sodium ampicillin, 15 mM HEPES (pH 7.2), and 10% (v/v) FCS. The cells were grown at 37° C. in a humid atmosphere of 5% $CO_2$ and 95% air and passaged every 3-4 days at a density of $6.0 \times 10^5$ cells/78-$cm^2$ plastic tissue culture dish (Corning). The DME was purchase Grand Island Biological and serum from K. C. Biologicals. All sera were used without heat inactivation.

Growth Factor Assay Methods

The growth factor specific activity in purified powders of kidney tissue was determined by a bioassay procedure which measures the growth response of MTW9/PL cells in serum-free Dulbecco's Modified Eagle's medium (DME). Tissue growth was followed up by the incorporation of tritium-labeled thymidine into DNA in response to varying concentrations of protein. Stock cultures used to initiate the assays were always used on day 3 after passage (counting day 0 as time of subculture); this procedure was essential since log phase cells were necessary for the assays of KDGF activity. Stock cultures (from 78-$cm^2$ dishes) were trypsin-treated briefly (2-4 minutes at room temperature) and the action of trypsin terminated by the addition of DME containing 10% (v/v) FCS. The detached cells were sedimented at $200 \times g$ for 5 min and resuspended in fresh DME containing 10% FCS. This stock was then diluted to $2.0 \times 10^4$ cells/ml in DME containing 10% (v/v) FCS and, with gentle stirring to keep the cells suspended evenly, 1.0-ml aliquots transferred to each of 24 wells in plastic cluster well tissue culture plates (Costar 3524, Cambridge, MA). The cells in the wells were then incubated for 24 hours at 37° C. in the $CO_2$ incubator to allow complete attachment and healing from the effects of trypsin; this incubation allowed the cells to begin undergoing metabolic processes. It must be noted that the period of incubation in FCS-containing medium is essential to the assay; if the cells are plated directly into serum-free medium in the wells, no KDGF growth factor activity is identified even with the most active preparations.

After 24 hours in serum-containing medium, the DME was removed from the cultures by gentle aspiration and replaced immediately (one well at a time) with 0.9 ml of serum-free DME. The plates were again incubated in a $CO_2$ atmosphere at 37° C. for exactly 24 hours, after which 0.1 ml of KDGF preparation was added. Growth factor dilutions were always made in serum-free DME. Incorporation of tritium-labeled thymidine was conducted for a two hour pulse-labeling period exactly at 22-24 hours after addition of KDGF. The labeled precursor ([methyl-$^3H$] thymidine, specific activity, 70 Ci/mmol, purchased from Schwarz/Mann) was added in 0.050-ml portions containing 1.0 uCi. Labeling was conducted at 37° C. in the humid $CO_2$ incubator. Thymidine incorporation was terminated by addition of 1.0 ml of Carnoy's fixative composed of three parts methanol and one part glacial acetic acid. Addition of this solution fixed the cells to the bottom of the culture wells and, by allowing the plates to stand for 3-5 hours, the soluble (non-DNA) pools of thymidine precursors were washed out. This fixing solution was then removed by aspiration, and each well was washed twice with 2.0 ml portions of 80% methanol (20% water) to remove all residual labeled thymidine. The methanol rinse was carried out with 24 wells per wash procedure. Then 0.3 ml of trypsin (1-300 hog pancreas preparation purchased from Nutritional Biochemicals) prepared at a concentration of 20 mg/ml in 50 mM HEPES (pH 7.3) was added to each well. After at least 2 hours at room temperature, 0.7 ml of 1% SDS prepared in distilled water was added to each well, and the total 1.0 ml from each well was transferred to scintillation vials. The radioactivity was determined in a Packard Tri-Carb Liquid Scintillation Spectrometer after addition of 10 ml/vial of Liquescent (National Diagnostics). The intra- and interassay variations in samples were usually 15% or less. Averages of either duplicate or triplicate wells were used in all cases.

The specific activity of both KDGF-I and KDGF-II preparations was estimated as the concentration of protein required to half replace the growth response of MTW9/PL cells to 10% (v/v) FCS. The incorporation of label in response to no additions (zero addition control) was designated $C_O$, while the incorporation of label in response to 10% FCS was designated $C_{10}$. The specific activity ($G_{50}$) was the arithmetic mean of these numbers; decreasing values represent a higher state of purity. A unit of KDGF activity was defined as that amount of protein which gave half replacement of the 10% FCS growth response. Throughout this study, protein concentrations were measured by the method of Bradford, M. *Analytical Biochemistry* 72:248-254 (1976), using bovine serum albumin as standard and reagents purchased from Bio-Rad Laboratories, Richmond, CA.

High Performance Liquid Chromatography Methods

All HPLC experiments were performed at room temperature with a Rainin Instruments Co., Inc., apparatus equipped with a variable wavelength detector, and computer controlled dual pumps allowing combinations of gradients to be employed in one elution. All solvents and other reagents used in the HPLC experiments were purchased from Burdick and Jackson, and were the highest quality available. The elution solvents were filtered and degassed just before use, and were not stored for long durations since the volatile components were lost within several days. All columns were pre-run without growth factor preparations over the same elution gradient as was used after KDGF samples were applied. This procedure ensured that any non-growth factor material that associated with the columns after several uses was eluted prior to sample application, and ensured that the KDGF preparations were not contaminated with other proteins during the HPLC run. The molecular sieve HPLC was done with a Spherogel TSK-2000 SW column (10±2 u particle size, 7.5 mm i.d.×600 mm l.) purchased from Beckman Scientific Instruments Division, and equilibrated and eluted with 0.1 M ammonium acetate (pH 5.1). The reverse phase ($C_{18}$ octyldecyl sialyl derivative, 10μ particle size diameter) HPLC was performed with a column purchased from Rainin Instruments, and equilibrated with 0.1% Trifluoroacetic Acid (TFA). The elution of KDGF from this column was done with an increasing isopropanol concentration gradient.

Source of Sheep Tissue for Purification

The lyophilized powder of mature ewe kidneys was a custom made product of the Waitaki Refrigerating Limited, Christchurch, New Zealand. The kidneys were collected in a day long process, stored on ice during this time, washed free of excess blood, and frozen. At a later time the frozen tissue was lyophilized, and the resulting material converted to a powder by treatment in a stainless steel ball mill. The powder represented 20 to 25% of the original weight of the kidneys. The KDGF activity was stable indefinitely when the powder was stored in a dry atmosphere at −20° C.

The following examples describe the purification schemes and the resultant estromedin kidney growth factors of the present invention.

EXAMPLE 1

Purification of Kidney Derived Growth Factor from Mature Ewe Kidney

Unless otherwise noted, all purification methods were done at 4° C. The basic 6 step procedure is detailed as follows.

Step 1.

A total of 500 grams of lyophilized kidney powder was added to 5 liters of 0.1 M acetic acid, and the mixture stirred for 24 hours. The suspension was clarified by centrifugation at 12,000×g for 60 min, and the supernatant filtered through glass wool to remove the floating lipid fraction. This crude extract was stored at −20° C. At later times the preparation was thawed at room temperature, and any precipitate removed by an additional centrifugation at 18,000×g for 30 minutes. The brown colored supernatant was adjusted to pH 4.5 with glacial acetic acid. The total volume was then 3815 ml.

Step 2

Aliquots of 200 ml from Step 1 were heated in a boiling water bath to a final solution temperature of 93° to 95° C. (10 minutes), then rapidly cooled to 0° C. in a propanol/dry ice bath. The large inactive precipitate was removed by centrifugation at 13,000×g for 30 minutes, and the active supernatant stored at −20° C. The preparation was then thawed and any precipitate removed by centrifugation as described above. The total volume at this point was 3575 ml.

Step 3.

Bio-Rad AG50W-X8 cation exchange resin was suspended in water for 30 min, and the resin washed by decantation 3 times in 10 volumes of 0.5 M sodium hydroxide. The settled resin was then washed 5 times with 10 volumes of water, suspended in 5 volumes of 1.0 M acetic acid, and finally washed 3 times in 5 volumes of 1.0 M acetic acid. The settled resin (20 ml) was added to the 3575 ml of heated supernatant, and the mixture stirred for 10 minutes at room temperature. The slurry was filtered through paper discs in a Buchner funnel, the resin discarded, and the active filtrate acidified to pH 2.9 with glacial acetic acid. Another aliquot (115 ml) of fresh washed resin was added to the acidified supernatant, and this mixture stirred overnight at 4° C. The resin was allowed to settle for 2 hours, and the inactive supernatant was poured off and discarded. The resin was washed successively with 250 ml of 1.0 M acetic acid, 120 ml of 0.1 M acetic acid, and finally 150 ml of 0.001 M acetic acid. The washes were inactive and were discarded. The resin was transferred to a 3.0 cm diameter glass column, and the KDGF activity eluted at room temperature with 10 mM ammonium hydroxide at a flow rate of 25 ml/hour. Fractions were collected, pooled, and lyophilized. The dried residue was dissolved in 50 ml of 10 mM sodium acetate buffer pH 5.8, and any precipitate removed by centrifugation at 13,000×g for 30 minutes. The sodium acetate buffers used in tnis step, and in subsequent steps, were prepared by neutralizing 10 mM acetic acid to the appropriate pH with concentrated sodium hydroxide.

Step 4

The pH 5.8 solution of KDGF from Step 3 was applied directly to a (4×52 cm) DEAE Sepharose CL-6B (Pharmacia Fine Chemicals) anion exchange column equilibrated in 10 mM sodium acetate pH 5.8. The column was then washed with 250 ml of the same 10 mM sodium acetate running buffer; the eluent contained no KDGF activity. Finally, the growth factor activity was eluted with a linear gradient of sodium chloride formed from 1 liter of running buffer and 1 liter of running buffer containing 0.5 M sodium chloride. The flow rate was 14 ml/hour, and 10.5 ml fractions were collected. KDGF activity was localized by using one hundred fold dilutions of each fraction in the tritium labeled thymidine assay. The data presented in FIG. 1 show the elution profile of the protein (i.e. 280 nm absorbance) and the position of KDGF activity elution. The highest specific activity fractions (88 through 106) were pooled and lyophilized. A total of 79 mg of protein was recovered from this step.

Step 5.

Figure 2:
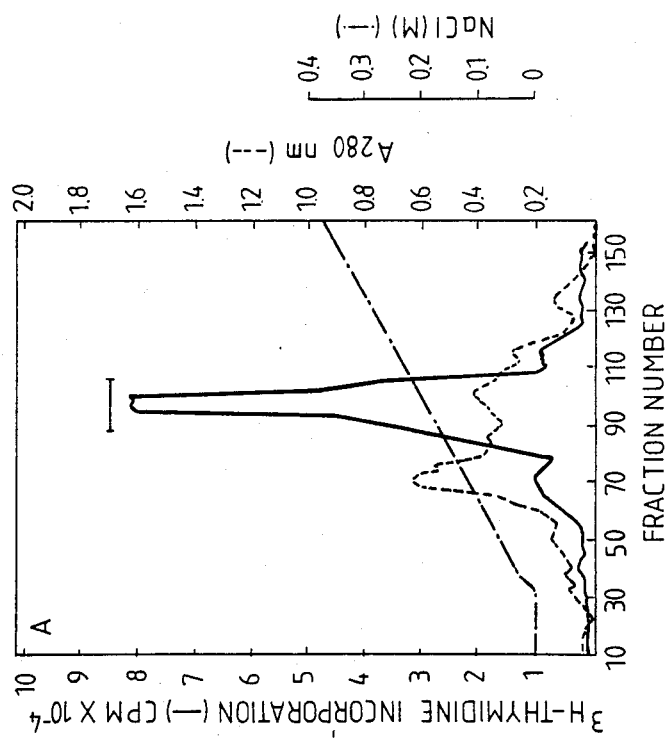
FIG. 2 - Elution profile of KDGF activity and protein from the DEAE-Sepharose CL-6B column equilibrated at pH 6.2, and eluted with a sodium chloride gradient as described in the text.

The lyophilized protein from Step 4 was redissolved in 20 ml of 10 mM sodium acetate, pH 6.2, and passed through a Sephadex G-25 superfine column (1×50 cm) equilibrated in the same buffer. This desalted preparation was next applied to another DEAE Sepharose CL-6B anion exchange column (3×38 cm) also equilibrated in the pH 6.2 sodium acetate buffer. The column was eluted with a linear gradient of 750 ml of running buffer and 750 ml of running buffer containing 0.3 M sodium chloride. The flow rate was 21 ml/hour, and 6 ml fractions were collected. KDGF activity was localized by one hundred fold dilutions of each fraction into the standard labeled precursor assay described in Experimental Procedures. FIG. 2 shows the elution profiles of the KDGF and the protein (280 nm absorbance) from the pH 6.2 DEAE column. Fractions 100 through 117 were pooled and lyophilized. A total of 24 mg of protein was recovered from the second DEAE chromatography.

Step 6.

Figure 3:
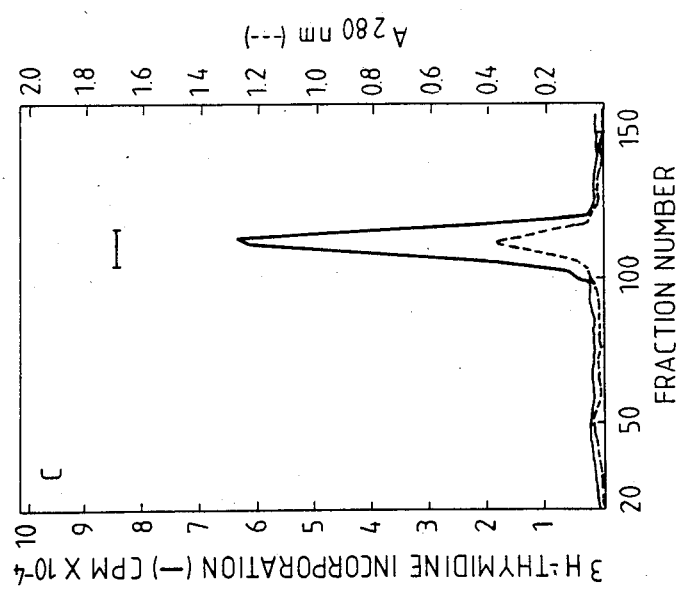
FIG. 3 - Elution profile of KDGF activity and protein from the Sephadex G-50 column eluted with acetic acid as described in the text.
Figure 4:
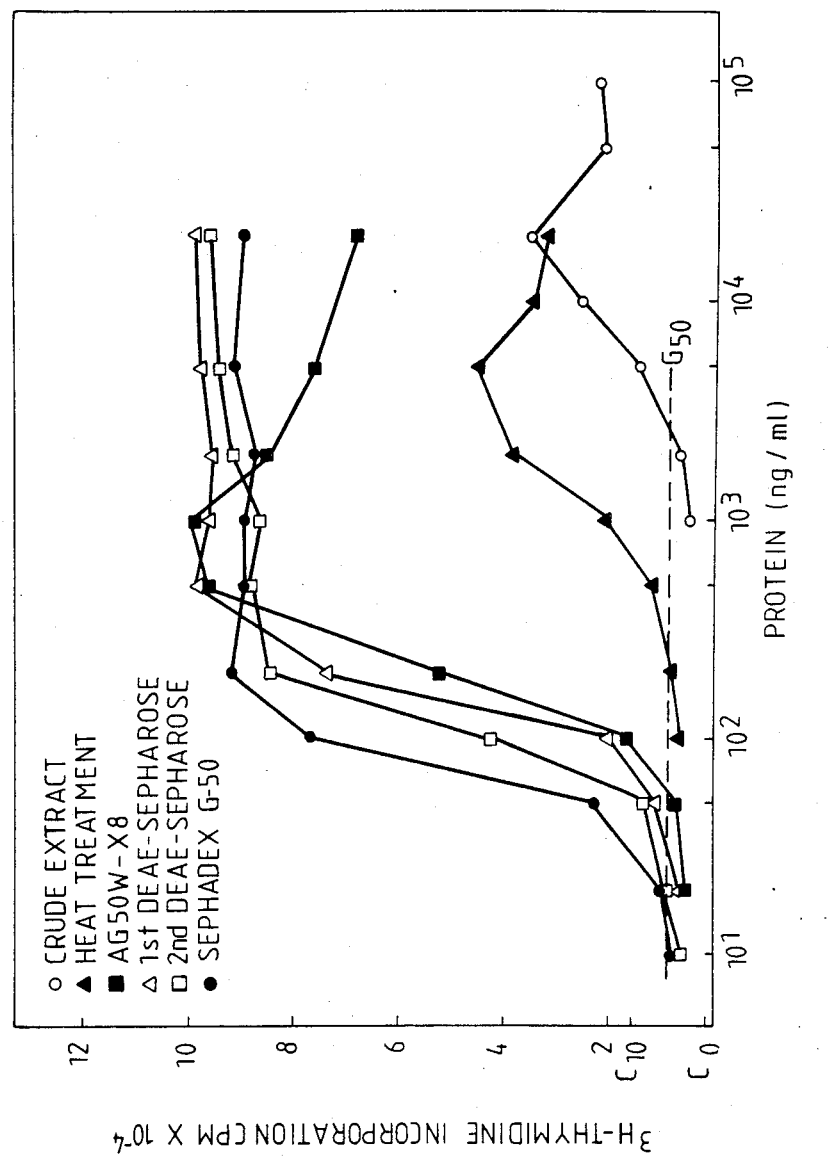
FIG. 4 - Assay of the KDGF activity in the pooled fractions from each step of the purification. The preparations were diluted in serum free DME, and a constant 100 ul of each dilution was added to the 0.9 ml assay mix of serum free DME. The designations of the data obtained with each pooled fraction are shown in the drawing.

The lyophilized KDGF preparation from Step 5 was dissolved in 20 ml of 0.1 M acetic acid, and applied to a Sephadex G-50 molecular sieve column (3.0×105 cm) equilibrated and eluted with 0.1 M acetic acid. Fractions (5.1 ml) were collected at a flow rate of 123 ml/hour. The elution profiles of KDGF activity and protein are shown in FIG. 3. The single peak of 280 nm absorbing material corresponded to the only fractions containing KDGF. Growth factor activity was localized by one hundred fold dilutions of each fraction into the usual labeled precursor incorporation bioassay. Fractions 105 through 118 were pooled and lyophilized. The final KDGF preparation was dissolved in 0.1 M acetic acid and stored in small aliquots at $-20°$ C. Under these conditions the activity was stable for several months.

purification procedure, the specific activity of each pooled fraction was monitored as shown in FIG. 4. The concentration of protein required to give a half maximal growth response ($G_{50}$) decreased with each purification step to a final level of 19 ng/ml ($4.5 \times 10^{-9}$ M). Also, from the data shown in FIG. 4, it was clear that high concentrations of all the fractions were able to saturate the growth response to the MTW9/PL cells in serum free DME, and that the saturation levels with the most purified fractions (i.e. steps 3 through 6) were well above the level of growth stimulated by 10% FCS ($C_{10}$). Based on the specific activity ($G_{50}$ of the initial acetic acid extract (FIG. 4), the final step 6 KDGF preparation was purified 142 fold.

At each step of the purification, amounts of 10 to 50 μg of protein were analyzed by the 8 M urea, 0.1% SDS PAGE. The results of these experiments were that Coomassie blue stained protein bands of $M_r$ ≈8,159 were found at all steps up to and including the first DEAE chromatography, and that no band corresponding to the purified growth factor was found until after the Bio-Rad AG50W-X8 step. A single Coomassie blue stained band was found even when amounts analyzed were up to 150 μg of protein per gel. Attempts were made to elute sliced discs from parallel unstained gels to demonstrate that the single protein band and the KDGF activity coincided. However, KDGF activity did not survive the boiling in 1.0% SDS used in sample preparation before electrophoresis. The apparent molecular weight of KDGF was calculated from a calibration curve constructed from the % relative mobilities of myoglobin and sequenced fragments of this protein in the urea, SDS gels, versus the log of their molecular weights. KDGF showed an estimated $M_r$ of 4,200.

Figure 5:
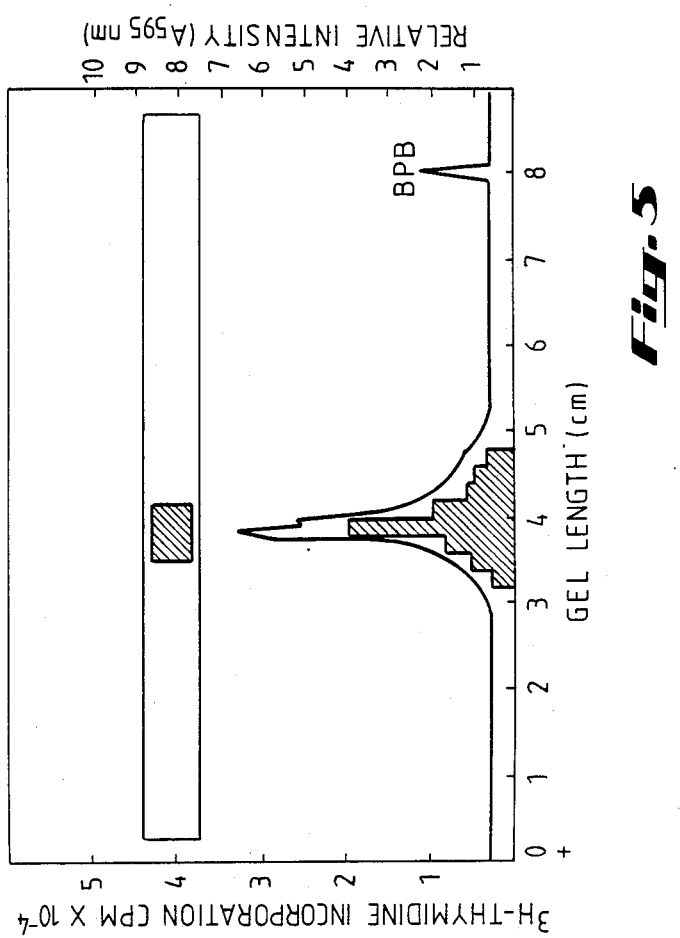

Analytical non-SDS PAGE was done at several different acrylamide gel concentrations (i.e. 5 to 15%) and over a range of pH from 2.9 to 8.5. An example of the results is presented in FIG. 5. PAGE at pH 2.9 in 15% acrylamide gels showed one major Coomassie blue stained band and the possible presence of another less abundant component when estimated by densitometry. This example was chosen for presentation since the conditions of the experiment in FIG. 5 represent the

TABLE 1

Purification of the mammary/pituitary/kidney tumor cell growth factor from lyophilized powder of mature ewe kidney.

| Step | Volume ml | Protein mg/ml | Total Protein mg | $G_{50}$ ng/ml | Total Activity units[a] | Purification fold | Yield % |
|---|---|---|---|---|---|---|---|
| Crude Extract[b] | 3815 | 8.29 | 31,625 | 2700 | $11.7 \times 10^6$ | 1 | 100 |
| Heat Treatment | 3575 | 0.88 | 3,146 | 310 | $10.1 \times 10^6$ | 8.7 | 86 |
| Bio-Rad AG50W-X8 | 50 | 5.69 | 285 | 58 | $4.9 \times 10^6$ | 46 | 42 |
| 1st DEAE pH 5.8 | 20 | 3.95 | 79 | 41 | $1.93 \times 10^6$ | 66 | 16 |
| 2nd DEAE pH 6.2 | 20 | 1.22 | 24 | 29 | $0.83 \times 10^6$ | 93 | 7 |
| Sephadex G-50 | 5 | 2.21 | 11 | 19 | $0.58 \times 10^6$ | 142 | 5 |

[a]A unit of activity is defined as the amount of protein that yield $G_{50}$ by the tritium labeled thymidine incorporation assay with MTW9/PL cells in completely serum free conditions.
[b]500 g of lyophilized sheep kidney powder was extracted with 5 liters of 0.1 M acetic acid as described in the text. This amount of powder corresponded to 2000 to 2500 g wet weight of kidney.

From the summary data shown in Table 1, it is apparent that substantial amounts of KDGF can be obtained by the methods applied. Amounts of only 500 g of lyophilized powder allowed preparation of 11 mg of growth factor, even though the overall activity yield was only 5%. Significant losses of activity occurred predominantly at steps 3 through 5, with approximate yields of 50% at each. Attempts to increase yields by substituting other methods have thus far led to reduced specific activities of the final products. Throughout the maximum attained separation of these proteins compared to all other non-SDS PAGE systems attempted. As is evident, the mobilities of the two components KDGF-I and KDGF-II are very similar. Elution of sliced discs of a parallel unstained gels showed that all of the KDGF activity corresponded to the densitometer localized position of the protein band in a companion stained gel. The total recovery of activity from the eluted gels was approximately 25%.

The degree of homogeneity of the KDGF Step 6 preparation was further characterized by analytical scale molecular sieve HPLC on a Spherogel-TSK 2000 SW column. The elution time of the KDGF activity was coincident with that of the only peak of material in the preparation that absorbed at 280 nm. From this data and from several other experiments done, no evidence of other non-KDGF components of different molecular weights was obtained, and no evidence of different molecular weight forms of KDGF could be found.

EXAMPLE 2

Cell Type Specificity of Purified KDGF

The range of cells promoted to grow by KDGF was examined. Since the factor was evaluated using an epithelial origin rat mammary tumor cell line that formed estrogen responsive tumors in host rats, KDGF was assayed for mitogenic activity with two other cell lines which have been shown previously to form estrogen responsive or dependent tumors in rodents. The cells used were the H-301 estrogen induced, and estrogen dependent Syrian hamster kidney line, and the estrogen responsive GH3/C14 rat pituitary tumor cells. KDGF proved to be a potent mitogen for the H-301 cells in serum free culture ($G_{50}$=75 ng/ml) although some 3 to 4 times less effective than for MTW9/PL cells.

The growth effect of KDGF was assayed on the GH3/C14 cells under two conditions. When growth factor was added to GH3/C14 cells cultures and pulse labeling with tritium labeled thymidine done after 48 hours, the $G_{50}$ value ranged from 5 to 10 µg/ml. When growth by DNA labeling was measured at 22 hours after growth factor addition, the apparent $G_{50}$ concentration of KDGF was reduced to 750 ng/ml. These data indicate that estrogen responsive pituitary cells increased the rate of DNA synthesis when KDGF was added to their serum free cultures, and that the time of DNA precursor pulse labeling dictated the apparent $G_{50}$ of a growth factor. Also, these data provide evidence that high concentrations of growth factor (i.e. greater than 5 µg/ml) can be used to identify responsive cells, which can then be reexamined at other labeling times to establish the $G_{50}$ at the optimum labeling period.

Using short term cultures of normal rat diploid fibroblasts, KDGF was shown not to be mitogenic at concentrations of up to 100 µg/ml. These data were in contrast to the effects readily identified on tumor origin cells, and suggest that the activity reported here is best classified as a tumor cell growth factor. Further exploration of this point was done with the cell line designated NRK (normal rat kidney). When used at a low passage number these cells behave as a normal, non-tumorigenic line, as evidenced by their low rates of colony formation in soft agar. This growth pattern facilitated wide spread use of the NRK cells as bioassay targets for alpha- and beta-transforming growth factors. The bioassay of transforming growth factors by soft agar colony formation was shown by others to require the additon of epidermal growth factor (EGF). At higher passage numbers, these cells progressively increase their capacity to form colonies in soft agar without requiring the presence of growth factor supplements to the usual serum containing medium. Using these properties, we have asked whether low and high passage NRK cells responded to KDGF both with and without added EGF. These experiments were conducted in serum free medium, since the presence of even low concentrations (i.e. 1%, vol/vol) of serum inhibited KDGF action. Also, the experiments were performed with non-confluent cultures (seed density $6.0\times 10^3$/multiwell), and at saturation densities (seed density $3.0\times 10^4$/multiwell) to determine whether density effects had a role in the regulation of responsiveness to KDGF. Neither KDGF alone nor EGF alone promoted growth (tritium labeled thymidine incorporation) of low passage NRK cells in confluent cultures. With non-confluent low passage number cultures limited mitogenic responses were seen to EGF alone but not KDGF alone, although cultures containing EGF (10 ng/ml) responded to very low concentrations (i.e. 0.05 ng/ml, or $1.2\times 10^{-11}$ M) KDGF. Thus with the relatively non-tumorigenic pheno-type NRK cells, KDGF and EGF were synergistic when cells were in sparse culture. Continuing with cultures of high passage NRK cells, the clear growth promoting effects of KDGF were demonstrated in confluent cultures, and with cells at low densities although the growth promoting effect was greater in sparse cultures. EGF and KDGF were synergistic growth promoters in low density cultures, as was found for the experiment in FIG. 11 C with low passage number NRK cells. In a final experiment, the growth promoting effects of EGF and/or KDGF were compared on LLCK-PK1 pig kidney cells. This line shows highly differentiated transport properties characterisitic of normal kidney tubule cells, was not tumorigenic in adult athymic nude mice, and as such may provide another way to characterize the KDGF activity. EGF alone was mitogenic for LLCK-PK1 cells, whereas KDGF was not. Also, KDGF and EGF were not synergistic in their action on these cells. Similar results were obtained with the dog origin MDCK kidney cell line which responded to EGF but not KDGF. As was the case with the LLCK-PK1 line, the MDCK cells have been shown to express normal kidney transport functions in culture, and shown low tumorgenicity in athymic nude mice.

EXAMPLE 3

KDGF Promotion of Growth Measured by Cell Number Increase

Since the growth factor was purified by monitoring activity as a function of precursor incorporation into DNA, it was important to establish action by cell number increase. This assay was done by inoculating the cells into dishes containing serum (10% FCS) supplemented medium for 24 hours to promote cell attachment, and then replacing the medium with serum free DME to which KDGF and other defined hormones and proteins were added; cell numbers were determined by Coulter Counte (Model ZB1) 6 days after initiating the serum free hormonally defined conditions.

Data presented in Table II confirm that in a serum free DME supplemented with insulin, EGF, transferrin, and a low concentration of fetuin (Peterson's Type III preparation purchased from Sigma) purified KDGF was a growth factor as defined by promoting cell number increase. It should be noted that KDGF alone did not cause cell replication, but that several factors are required for the overall process.

TABLE II

KDGF mitogenic activity with MTW9/PL cells as measured by cell number increase.

| ADDITIONS | CELLS PER PLATE AFTER 3 DAYS[a] |
|---|---|
| DME ONLY (NO SERUM OR GROWTH FACTORS) | $6.2 \times 10^{4[b][c]}$ |
| 10% (vol/vol) FCS | $50.8 \times 10^4$ |
| KDGF IN SERUM FREE DME[e] | $6.0 \times 10^4$ |
| EGF + F + I + T[e] | $11.0 \times 10^{4[b][d]}$ |
| KDGF + EGF + F + I = T[e] | $33.1 \times 10^{4[c][d]}$ |

[a]The standard deviations of duplicate or triplicate samples were ± 15% or less.
[b]Statistical analysis by students T test showed differences significant to p≤0.01.
[c][d]Statistical analysis by students T test showed differences significant to p≤0.001.
[e]The concentrations of the components added to serum free DME were KDGF, 100 ng/ml; EGF, 10 ng/ml; fetuin (F), 10 ug/ml; insulin (I), 5 ug/ml; and transferrin (T), 5 ug/ml.

EXAMPLE 4

Effect of Reducing Agents on the Molecular Weight and Biological Activity of KDGF Treatment of Step 6 KDGF with either 5% 2-mercaptoethanol or up to 50 mM dithiothreitol at neutral pH had no effect on the apparent molecular weight of KDGF as estimated by 8 M urea, 0.1% SDS PAGE. The same apparent molecular weight of 4,200 daltons was confirmed both before and after reducing agent treatment. When the biological activity of untreated KDGF was compared to that of 2-mercaptoethanol or dithiothreitol treated KDGF, these agents had no effect on the growth factor activity.

EXAMPLE 5

Separation of KDGF into KDGF-I and KDGF-II by Chromatofocusing

To determine the isoelectric point of Step 6 KDGF, the preparation was submitted to chromatofocusing (Pharmacia) over the range pH 6.3 to 4.0. Elution of the column showed two well separated protein peaks (i.e. 280 mm absorbing materials), and bioassay of each of the fractions collected showed KDGF activity in both peaks. Combined, the activity in both peaks represented greater than 80% recovery of the applied KDGF. The two peaks were pooled separately, and designated KDGF-I and KDGF-II with pIs 5.2 and 4.8, respectively. KDGF-II was 70% of the total recovered growth factor activity, and approximately 80% of the total protein recovered as estimated by the Bradford procedure. Since it was possible that the two forms of KDGF were generated by partial (proteolytic) degradation or some other unrecognized modification during sample preparation and running, each isolated peak was reexamined again by 8 M urea, 0.1% SDS PAGE to determine if changes in molecular weight had occurred. Experiments confirmed that within the limits of ±200 daltons, no change in $M_r$ 4,200 was detected compared to the original KDGF, and no differences in $M_r$ were found between KDGF-I and KDGF-II. Analysis by non-SDS PAGE at pH 2.9, showed no changes in electrophoretic mobility KDGF-I and KDGF-II compared to the original Step 6 KDGF preparation.

Bioassays of the growth promoting activities of KDGF-I and KDGF-II were done with MTW9/PL cells. KDGF-I showed a $G_{50}$ of 10 ng/ml ($2.4 \times 10^{-9}$ M) while KDGF-II gave a somewhat higher value of 19 ng/ml. As described above, Step 6 KDGF showed a $G_{50}$ of 19 ng/ml (Table I) which was consistent with this preparation being 80% or more KDGF-II.

Comparisons of the susceptibility of KDGF-I and KDGF-II to trypsin and pronase digestion were done to confirm the peptide nature of the activities and to determine whether major differences in protease sensitivity could be found. Both KDGF-I and KDGF-II activities were greater than 90% lost within 2 hours of incubation at 25° C. with immobilized pronase. Immobilized trypsin treatment at 25° C. for 4 hours resulted in approximately 50% loss of the biological activity of both factors, followed by a much slower rate of loss. Since both KDGFs showed similar kinetics of activity loss with trypsin digestion, there may be structural similarities between these growth factors. This possibility was further supported by the data showing that 25 to 50% of the original activity remained for both factors even after prolonged incubation with trypsin. Also, these data suggested the possibility that a smaller biologically active peptide core might have been formed, and that this activity was highly trypsin resistant.

EXAMPLE 7

Reverse Phase HPLC Separation of KDGF-I and KDGF-II

The two forms of KDGF separated by chromatofocusing were further analyzed for homogeneity by reverse phase HPLC on a $C_{18}$ sialyl column equilibrated in 0.1% trifluoroacetic acid (TFA) and eluted with increasing concentrations of isopropanol in the TFA. KDGF-II appeared to be a single component eluting at a retention time of 31.5 minutes. The activity and absorbance at 280 nm coincided in the eluate fractions. An identical experiment with KDGF-I showed one major peak eluting at 24.8 min and a second at 26.5 minutes. Bioassays showed that both peaks may have possessed growth factor activity, but that the earlier eluting peak (i.e. 24.8 minutes) had the greater activity. In going back through the fractions of the purification to determine when these forms first became clearly distinguishable, the pooled fractions from the pH 6.2 DEAE-Sepharose column (Step 5) contained both types of KDGF as analyzed by reverse phase HPLC. The material isolated at this stage of the purification contained $A_{280nm}$ peaks and KDGF activity peaks that corresponded to the sum of KDGF-I and KDGF-II chromatographic profiles.

EXAMPLE 8

Amino Acid Composition of KDGF-I and KDGF-II

The separated peaks corresponding to KDGF-I and KDGF-II were analyzed by standard 6 N hydrochloric acid hydrolysis at 120° C. followed by phenylthiohydantoin derivatization and quantitation by HPLC. The results are presented in Table III. Amino acid analysis of KDGF-I and KDGF-II showed both qualitative and quantitative similarities in these 2 factors. There were more acidic (aspartic and glutamic) acid residues in each than basic residues (lysine and arginine), which was consistant with the acidic isoelectric points of both of these mitogens. Also, the analysis data showed that KDGF-I may be a less homogeneous preparation than KDGF-II, which was consistent with the HPLC data.

TABLE III

Amino Acid Compositions of KDGF-I and KDGF-II.

| AMINO ACID RESIDUE | KDGF-I (moles/mole proline) | KDGF-II (moles/mole proline) |
|---|---|---|
| Alanine | 1.69 | 2.08 |
| Arginine | 0.73 | 0.89 |
| Aspartic Acid | 3.37 | 3.65 |
| Glutamic Acid | 3.39 | 3.90 |
| Glycine | 0.89 | 0.80 |
| Half cystine | 0.49 | 0.52 |
| Histidine | 0.20 | 0.34 |
| Isoleucine | 0.50 | 0.52 |
| Leucine | 1.56 | 2.11 |
| Lysine | 1.67 | 2.22 |
| Methionine | 0.11 | 0.09 |
| Phenylalanine | 0.81 | 0.95 |
| Proline | 1.00 | 1.00 |
| Serine | 0.99 | 1.09 |
| Threonine | 0.94 | 0.88 |
| Tryptophan | n.d.* | n.d.* |
| Tyrosine | 0.61 | 0.97 |
| Valine | 1.16 | 1.53 |

*n.d. indicates the determination was not done.

UTILITY

The basic findings of this invention are that a class of estrogen inducible polypeptide growth factors (endocrine and autocrine estromedins) are involved in mammary, pituitary, uterine, and kidney tumor cell growth in experimental animals and humans. Several of these low molecular weight peptides have been isolated in substantial amounts from normal mammalian estrogen target tissues and from estrogen responsive tumors or cells in culture. These activities have been shown to share many common biochemical biological properties, but in at least some cases the molecular species are different.

Since the activities thus far isolated all show potent growth factor activity with human breast cancer cells, and since relatively large amounts of these factors can be purified by our methods, the use of these activities in the treatment and diagnosis of breast and other hormone responsive cancers is an important application.

Polyclonal and monoclonal antibodies to these growth factors can be used to develop specific radioimmunoassay (RIA) methods of measurement for screening plasma and urine samples of patients suspected of having estrogen inducible tumors, and to develop screening methods for determining those females at potentially greater risk of expressing these cancers than the general population. Human monoclonal antibodies to either the growth factors or their serum binding proteins are potential therapeutic reagents which can be used to eliminate the mitogenic activities from the circulation or the immediate microenvironment of tumors.

Fluorescent labeled antibodies (second antibodies) can be used in laboratory pathology for diagnostic examination of biopsy tissue to determine the increased production of growth factors by tumor cells over the substantially lower concentrations found in normal tissues. Since continual production of tumor cell growth factors is known to occur, the RIA method of measuring the plasma concentration may serve an important role in monitoring the effectiveness of a chemotherapy protocol or radiation treatments.

The antibodies according to the invention can be prepared in a variety of ways known in the art, depending on whether monoclonal or polyclonal antibodies are desired. For polyclonal antibodies, a vertebrate, typically a domestic animal, is hyperimmunized with antigen and the blood collected shortly after repeat imunizations and the gamma globulin isolated. Suitable methods for preparing polyclonal antibodies are described in the Handbook of Experimental Immunology, 3rd edition, Weir, Editor, Blackwell Scientific Publications, Oxford and London, 1978. For monoclonal antibodies, a small animal, typically a mouse or rat, is hyperimmunized with antigen, the spleen removed and the lymphocytes fused with myeloma cells in the presence of a suitable fusion promoter. The resulting hybrid cells or hybridomas are screened to isolate individual clones, each of which secrete a single antibody species to the antigen. The individual antibody species obtained in this way are each the product of a single B cell from the immune animal generated in response to a specific antigenic site recognized on the immunogenic substance. The general process for obtaining monoclonal antibodies, including those according to the invention, is described by Kohler and Milstein (1975) Nature 256, pp. 495–497. The Growth Factor peptides and antigenic oligopeptides, that is antigenic peptide fragments of the Growth Factor peptides of the invention, used to produce antibodies (both polyclonal and monoclonal) may be employed directly in the immunization procedure or they may be bound to a suitable carrier-protein using methods known in the art, for example, see U.S. Pat. No. 4,341,761 to Ganfield et al. Use of a carrier protein part larly preferred when the immunization is carried out using the antigenic oligopeptides of the invention.

The antibodies according to the invention may be used in a variety of ways. In a preferred application, they may be used for diagnosis of malignancy and other proliferative diseases. In instances where the antigen may be found in a physiological fluid or at a concentration differential only when malignancy or other proliferative disease exists, the physiological fluid, such as serum, plasma, whole blood or cerebrospinal fluid may be assayed. Antibodies employed in assays may be labeled or unlabeled. Unlabeled antibodies may be employed in agglutination; labeled antibodies may be employed in a wide variety of assays, employing a wide variety of labels, such as radionuclides, enzymes, fluorescers, enzyme substrates or cofactors, or the like. These techniques are amply defined in the literature and exemplary assays may be found in U.S. Pat. Nos. 3,817,834, 3,935,074, 4,233,402 and 4,318,980, as illustrative.

In some techniques it will be useful to label the antigen or fragment thereof, rather than the antibody, and have a competition between labeled antigen and antigen in the sample for antibody. In this situation, it is common to provide kits which have the combination of the labeled antigen or labeled fragment and the antibody in amounts which provide for optimum sensitivity and accuracy. In other situations, it is desirable to have a solid support, where either antigen or antibody is bound. A polyepitopic antigen can serve as a bridge between antibody bound to a support and labeled antibody in the assay medium. Alternatively, one may have a competition between labeled antigen and any antigen in the sample for a limited amount of antibody.

Where the antigen may not be found in a physiological fluid or if found there is not diagnostic of malignancy or the target proliferative disease, then cells will have to be isolated and the cells assayed for the presence of the antigen. For detecting the antigen, the tissue sample may be lysed by conventional methods, e.g., base, detergents, or the like, cellular debris separated by filtration or centrifugation and the filtrate or supernatant isolated and assayed.

For purposes of therapy, either xenogeneic or allogeneic antibodies may be employed, depending upon the nature of the treatment, and whether the foreign antibodies will induce an immune response. The literature has described a number of ways of making human antibodies, where it is found that mouse or other mammalian antibodies are not satisfactory. The antibodies may be used in a wide variety of ways. By employing the appropriate IgG (other than $IgG_1$), one may induce lysis through the natural complement process. Alternatively, the lysing portion of a toxin may be joined to the antibodies, particularly a Fab fragment. The antibodies may be bound to liposomes for directing the liposomes to the malignant cells to become ingested by the cells by merging of the membranes. Other labels may also be bound to the antibodies, such as radionuclides, fluorescers, enzymes, and the like. By introducing the antibodies in vivo, the antibodies will direct the label to the malignant cell, where the presence of malignancy may be diagnosed or treated.

The formulation of the antibodies will vary widely, depending on the nature of the label, the purpose of the antibodies, the site to which the antibodies are to be directed, and the like. Usually, the antibodies will be formulated in a physiologically acceptable carrier, e.g. saline or phosphate buffered saline, and injected into the host, when possible at the desired site, and when this is not possible, into a circulating system, such as blood.

Methods and compositions employing the growth factor peptides and oligopeptides of the invention are also afforded for treatment of cancer and other proliferative diseases and for therapies wherein cell growth promotion is beneficial, e.g., wound healing and ulcer therapy. These therapeutic compositions comprise effective amounts of the indicated peptides in a mixture with pharmaceutically acceptable carriers. In particular, pharmaceutical compositions that contain the peptides of the invention as an active ingredient will normally be formulated with an appropriate solid or liquid carrier depending upon the particular mode of administration being used. For instance, parenteral formulations are usually injectable fluids that use pharmaceutially and physiologically acceptable fluids such as physiological saline, balanced salt solutions, or the like as a vehicle. Oral formulations, on the other hand, may be solid, e.g., tablet or capsule, or liquid solutions or suspensions.

In the therapeutic methods of the invention, the peptides may be administered to humans in various manners such as orally, intravenously, intramuscularly, intraperitoneally, intranasally, intradermally, and subcutaneously. The particular mode of administration and dosage regimen will be selected by the attending physician taking into account the particulars of the patient, the nature of treatment required, and/or the disease and the disease state involved. For instance, damaged tissue from wounds is usually treated by daily or twice daily doses over a few days to a few weeks; whereas tumor or cancer treatment involves daily or multidaily doses over months or years. The oligopeptide and/or peptide therapy of the invention may be combined with other treatments and may be combined with or used in association with other chemotherapeutic or chemopreventive agents for providing therapy against proliferative diseases, neoplasms, or other conditions against which they are effective.

In addition to these uses of the growth factor and antibodies to these activities, the growth factor will be used to isolate the cell surface receptor proteins which will provide another valuable approach to therapy. Human monoclonal antibodies to the growth factor receptor can be used to block growth factor action, and hence provide a highly specific means of inhibiting further tumor growth. This approach to tumor therapy may avoid many of the problems of conventional cancer treatments which often have debilitating side effects.

While the invention has been described in terms of preferred embodiments constituting the best mode known to applicants at the time of this application, various changes may be made in the invention without departing from the scope thereof which is defined by the following claims.

What is claimed is:

1. A substantially pure peptide growth factor prepared by a process comprising the steps of:

lyophilizing an estrogen responsive kidney tissue sample;

extracting said sample with an aqueous solution of acetic acid;

heating the resulting extract from about 93° C. to about 95° C. followed by centrifugation to remove any proteolytic activity and other major impurities;

subjecting said extract to DEAE Sepharose cation exchange chromatography equilibrated at about pH 5.8 followed by further lyophilization;

redissolving said lyophilized extract in a buffer solution at a pH of about 6.2 and subjecting said extract to further DEAE Sephadex anion exchange chromatography;

collecting a 3000-6000 molecular weight fraction from the resulting extract using a Sephadex G-50 molecular sieve column, and chromatofocusing the 3000-6000 molecular weight fraction to yield a KDGF-I and a KDGF-II fraction both having an apparent molecular weight of 4200 daltons.

2. A substantially pure peptide growth factor termed KDGF-I characterized by:

(a) an estimated molecular weight of 4200±200 daltons;
(b) a pI of 5.2 +0.2;
(c) derived from estrogen responsive kidney tissue;
(d) eluting at 24.8 minutes by reverse phase HPLC on a $C_{18}$ sialyl column equilibrated in 0.1% trifluoroacetic acid and eluted with increasing concentrations of isopropanol in the trifluoroacetic acid;
(e) lacking intra and intermolecular disulfide bonding; and
(f) having an amino acid composition on a moles/mole proline approximating:

| | |
|---|---|
| Alanine | 1.69 |
| Arginine | 0.73 |
| Aspartic Acid | 3.37 |
| Glutamic Acid | 3.39 |
| Glycine | 0.89 |
| Half cystine | 0.49 |
| Histidine | 0.20 |
| Isoleucine | 0.50 |
| Leucine | 1.56 |
| Lysine | 1.67 |
| Methionine | 0.11 |

-continued

| | |
|---|---|
| Phenylalanine | 0.81 |
| Proline | 1.00 |
| Serine | 0.99 |
| Threonine | 0.94 |
| Tryptophan | n.d.* |
| Tyrosine | 0.61 |
| Valine | 1.16 |

*n.d. indicates the determination was not done.

3. A substantially pure peptide growth factor termed KDGF-II characterized by:
 (a) an estimated molecular weight of 4200±200 daltons;
 (b) a pI of 4.8±0.2;
 (c) derived from estrogen responsive kidney tissue;
 (d) eluting at 31.5 minutes by reverse phase HPLC on a $C_{18}$ sialyl column equilibrated in 0.1% trifluoroacetic acid and eluted with increasing concentrations of isopropanol in the trifluoroacetic acid;
 (e) lacking intra and intermolecular disulfide bonding, and
 (f) having an amino acid composition on a moles/moles proline approximating:

| | |
|---|---|
| Alanine | 2.08 |
| Arginine | 0.89 |
| Aspartic Acid | 3.65 |
| Glutamic Acid | 3.90 |
| Glycine | 0.80 |
| Half cystine | 0.52 |
| Histidine | 0.34 |
| Isoleucine | 0.52 |
| Leucine | 2.11 |
| Lysine | 2.22 |
| Methionine | 0.09 |
| Phenylalanine | 0.95 |
| Proline | 1.00 |
| Serine | 1.09 |
| Threonine | 0.88 |
| Tryptophan | n.d.* |
| Tyrosine | 0.97 |
| Valine | 1.53 |

*n.d. indicates the determination was not done.

* * * * *